(12) United States Patent
Viola

(10) Patent No.: US 8,435,203 B2
(45) Date of Patent: May 7, 2013

(54) GASTRIC RESTRICTOR ASSEMBLY AND METHOD OF USE

(75) Inventor: Frank J. Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 1409 days.

(21) Appl. No.: 11/820,878

(22) Filed: Jun. 20, 2007

(65) Prior Publication Data

US 2008/0319470 A1 Dec. 25, 2008

(51) Int. Cl.
*A61M 39/00* (2006.01)
*A61F 2/00* (2006.01)
*A61F 2/02* (2006.01)
*A61M 39/10* (2006.01)
*A61F 2/04* (2006.01)
*A61F 2/82* (2006.01)
*A61F 2/84* (2006.01)

(52) U.S. Cl.
USPC ........... 604/9; 604/8; 604/93.01; 604/164.01; 604/164.04; 623/23.64; 623/23.65

(58) Field of Classification Search .......... 604/8, 93.01; 623/23.64, 23.65; 606/151, 153
See application file for complete search history.

(56) References Cited

U.S. PATENT DOCUMENTS

| | | | | |
|---|---|---|---|---|
| 3,574,865 A | * | 4/1971 | Hamaker | 623/2.34 |
| 4,476,863 A | * | 10/1984 | Kanshin et al. | 606/153 |
| 4,598,712 A | * | 7/1986 | Rebuffat et al. | 606/153 |
| 5,290,298 A | * | 3/1994 | Rebuffat et al. | 606/153 |
| 5,346,501 A | * | 9/1994 | Regula et al. | 606/151 |
| 5,360,154 A | * | 11/1994 | Green | 227/179.1 |
| 5,425,738 A | * | 6/1995 | Gustafson et al. | 606/153 |
| 5,522,885 A | * | 6/1996 | Love et al. | 623/2.11 |
| 6,059,827 A | * | 5/2000 | Fenton, Jr. | 623/2.17 |
| 6,254,642 B1 | * | 7/2001 | Taylor | 623/23.64 |
| 6,358,228 B1 | | 3/2002 | Tubman et al. | |
| 6,400,980 B1 | | 6/2002 | Lemelson | |
| 6,413,274 B1 | * | 7/2002 | Pedros | 623/2.11 |
| 6,419,699 B1 | | 7/2002 | Schuessler | |
| 6,427,089 B1 | | 7/2002 | Knowlton | |
| 6,432,039 B1 | | 8/2002 | Wardle | |
| 6,432,040 B1 | | 8/2002 | Meah | |
| 6,449,512 B1 | | 9/2002 | Boveja | |
| 6,450,173 B1 | | 9/2002 | Forsell | |
| 6,450,946 B1 | | 9/2002 | Forsell | |
| 6,453,907 B1 | | 9/2002 | Forsell | |
| 6,454,698 B1 | | 9/2002 | Forsell | |
| 6,454,699 B1 | | 9/2002 | Forsell | |
| 6,454,700 B1 | | 9/2002 | Forsell | |

(Continued)

FOREIGN PATENT DOCUMENTS

| | | |
|---|---|---|
| WO | WO2004/041133 A | 5/2004 |
| WO | WO2005/120363 A | 12/2005 |

OTHER PUBLICATIONS

European Search Report for EP 08252043.8-2310 date of completion is Oct. 22, 2008 (8 pages).

*Primary Examiner* — Leslie Deak
*Assistant Examiner* — Adam Marcetich

(57) ABSTRACT

A gastric restrictor assembly is provided. The assembly includes a housing defining a throughbore and having a base portion, a waist portion and head portion. The assembly also includes a pin holder including a plurality of pins extending therefrom. The pin holder is configured for being lockingly received within the housing. The plurality of pins extend across the waist portion when the pin holder is received within the housing.

16 Claims, 10 Drawing Sheets

U.S. PATENT DOCUMENTS

| | | |
|---|---|---|
| 6,454,701 B1 | 9/2002 | Forsell |
| 6,454,785 B2 | 9/2002 | Dehoyos Garza |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,698 B1 | 10/2002 | Falwell |
| 6,471,635 B1 | 10/2002 | Forsell |
| 6,494,879 B2 | 12/2002 | Lennox et al. |
| 6,500,110 B1 | 12/2002 | Davey et al. |
| 6,511,490 B2 | 1/2003 | Robert |
| 6,511,506 B2 | 1/2003 | Chevillon et al. |
| 6,540,789 B1 | 4/2003 | Silverman et al. |
| 6,543,456 B1 | 4/2003 | Freeman |
| 6,547,801 B1 | 4/2003 | Dargent et al. |
| 6,558,400 B2 | 5/2003 | Deem et al. |
| 6,572,627 B2 | 6/2003 | Gabbay |
| 6,579,225 B2 | 6/2003 | Pregenzer et al. |
| 6,587,719 B1 | 7/2003 | Barrett et al. |
| 6,596,004 B1 | 7/2003 | Regnault |
| 6,609,025 B2 | 8/2003 | Barrett et al. |
| 6,627,206 B2 | 9/2003 | Lloyd |
| 6,652,448 B2 | 11/2003 | Migachyov |
| 6,656,194 B1 | 12/2003 | Gannoe et al. |
| 6,666,817 B2 | 12/2003 | Li |
| 6,675,809 B2 | 1/2004 | Stack et al. |
| 6,676,674 B1 | 1/2004 | Dudai |
| 6,726,696 B1 | 4/2004 | Houser et al. |
| 6,730,014 B2 | 5/2004 | Wilk |
| 6,740,121 B2 | 5/2004 | Geitz |
| 6,746,460 B2 | 6/2004 | Gannoe et al. |
| 6,752,754 B1 | 6/2004 | Feng et al. |
| 6,755,869 B2 | 6/2004 | Geitz |
| 6,758,219 B2 | 7/2004 | Sapala et al. |
| 6,773,440 B2 | 8/2004 | Gannoe et al. |
| 6,773,441 B1 | 8/2004 | Laufer et al. |
| 6,776,789 B2 | 8/2004 | Bryant et al. |
| 6,790,214 B2 | 9/2004 | Kraemer et al. |
| 6,802,868 B2 | 10/2004 | Silverman et al. |
| 6,808,483 B1 | 10/2004 | Ortiz et al. |
| 6,826,428 B1 | 11/2004 | Chen et al. |
| 2001/0011543 A1 | 8/2001 | Forsell |
| 2001/0034470 A1 | 10/2001 | Whalen et al. |
| 2002/0022851 A1 | 2/2002 | Kalloo et al. |
| 2002/0028979 A1 | 3/2002 | Silverman et al. |
| 2002/0052538 A1 | 5/2002 | Lau et al. |
| 2002/0065449 A1 | 5/2002 | Wardle |
| 2002/0091395 A1 | 7/2002 | Gabbay |
| 2002/0116013 A1 | 8/2002 | Gleason et al. |
| 2002/0151763 A1 | 10/2002 | Cook et al. |
| 2002/0169464 A1 | 11/2002 | Latour |
| 2002/0183768 A1 | 12/2002 | Deem et al. |
| 2002/0188354 A1 | 12/2002 | Peghini |
| 2002/0198548 A1 | 12/2002 | Robert |
| 2003/0032857 A1 | 2/2003 | Forsell |
| 2003/0040804 A1 | 2/2003 | Stack et al. |
| 2003/0040808 A1 | 2/2003 | Stack et al. |
| 2003/0088148 A1 | 5/2003 | Forsell |
| 2003/0092962 A1 | 5/2003 | Forsell |
| 2003/0109931 A1 | 6/2003 | Geitz |
| 2003/0120288 A1 | 6/2003 | Benchetrit |
| 2003/0130670 A1 | 7/2003 | Anderson et al. |
| 2003/0144575 A1 | 7/2003 | Forsell |
| 2003/0158564 A1 | 8/2003 | Benchetrit |
| 2003/0158569 A1 | 8/2003 | Wazne |
| 2003/0158601 A1 | 8/2003 | Silverman et al. |
| 2003/0171768 A1 | 9/2003 | McGhan |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208212 A1 | 11/2003 | Cigaina |
| 2003/0212306 A1 | 11/2003 | Banik |
| 2003/0225311 A1 | 12/2003 | Sayet et al. |
| 2004/0006351 A1 | 1/2004 | Gannoe et al. |
| 2004/0030347 A1 | 2/2004 | Gannoe et al. |
| 2004/0039452 A1 | 2/2004 | Bessler |
| 2004/0044357 A1 | 3/2004 | Gannoe et al. |
| 2004/0045562 A1 | 3/2004 | Sapala et al. |
| 2004/0049209 A1 | 3/2004 | Genchetrit |
| 2004/0059289 A1 | 3/2004 | Garza Alvarez |
| 2004/0082963 A1 | 4/2004 | Gannoe et al. |
| 2004/0089313 A1 | 5/2004 | Utley et al. |
| 2004/0092974 A1 * | 5/2004 | Gannoe et al. ................. 606/153 |
| 2004/0093091 A1 | 5/2004 | Gannoe et al. |
| 2004/0097989 A1 | 5/2004 | Molina Trigueros |
| 2004/0107004 A1 | 6/2004 | Levine et al. |
| 2004/0116773 A1 | 6/2004 | Furness et al. |
| 2004/0117031 A1 | 6/2004 | Stack et al. |
| 2004/0122455 A1 | 6/2004 | Lin |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133219 A1 | 7/2004 | Forsell |
| 2004/0138684 A1 | 7/2004 | Eton |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0147810 A1 | 7/2004 | Mizuno |
| 2004/0158272 A1 | 8/2004 | Hofle et al. |
| 2004/0158331 A1 | 8/2004 | Stack et al. |
| 2004/0167561 A1 | 8/2004 | Boucher et al. |
| 2004/0172141 A1 | 9/2004 | Stack et al. |
| 2004/0172142 A1 | 9/2004 | Stack et al. |
| 2004/0199196 A1 | 10/2004 | Ravo |
| 2004/0204722 A1 | 10/2004 | Sikora et al. |
| 2004/0204768 A1 | 10/2004 | Geitz |
| 2004/0209538 A1 | 10/2004 | Klinge et al. |
| 2004/0210243 A1 | 10/2004 | Gannoe et al. |
| 2004/0220682 A1 | 11/2004 | Levine et al. |
| 2004/0230137 A1 | 11/2004 | Mouton |
| 2004/0243152 A1 | 12/2004 | Taylor et al. |
| 2004/0254537 A1 | 12/2004 | Conlon et al. |
| 2004/0260316 A1 | 12/2004 | Knudson et al. |
| 2004/0267293 A1 | 12/2004 | Byrum et al. |
| 2005/0004430 A1 | 1/2005 | Lee et al. |
| 2005/0004681 A1 | 1/2005 | Stack et al. |
| 2005/0038458 A1 | 2/2005 | Bailly et al. |
| 2005/0049718 A1 | 3/2005 | Dann et al. |
| 2005/0055039 A1 | 3/2005 | Burnett et al. |
| 2005/0070931 A1 | 3/2005 | Li et al. |
| 2005/0075652 A1 | 4/2005 | Byrum et al. |
| 2005/0080317 A1 | 4/2005 | Merade |
| 2005/0085688 A1 | 4/2005 | Girard et al. |
| 2005/0085835 A1 | 4/2005 | Rennich |
| 2005/0085923 A1 | 4/2005 | Levine et al. |
| 2005/0090844 A1 | 4/2005 | Patel et al. |
| 2005/0096673 A1 | 5/2005 | Stack et al. |
| 2005/0228442 A1 * | 10/2005 | Wheatley et al. ............. 606/213 |
| 2006/0085017 A1 * | 4/2006 | Borghi .......................... 606/153 |
| 2006/0253142 A1 * | 11/2006 | Bjerken ........................ 606/153 |
| 2006/0264982 A1 * | 11/2006 | Viola et al. ................... 606/153 |
| 2006/0264983 A1 * | 11/2006 | Holsten et al. ................. 606/153 |
| 2007/0010834 A1 * | 1/2007 | Sharkawy et al. ............ 606/153 |
| 2008/0015617 A1 * | 1/2008 | Harari et al. .................. 606/153 |

* cited by examiner

GASTRIC RESTRICTOR ASSEMBLY AND METHOD OF USE

BACKGROUND

1. Technical Field

The present disclosure relates to a surgical implant for treating obesity in a patient. More particularly, the present disclosure relates to a surgical implant for constricting the stomach in a patient to treat obesity of a patient.

2. Background of Related Art

A variety of different approaches are known for the treatment of obesity in a patient. These approaches can be of the non-surgical variety, e.g., dieting and exercise, or of the surgical variety, e.g., gastric bypass, bilo-pancreatic diversion etc. Where non-invasive non-surgical procedures such as dieting rely on the will power of the patient and may not be effective, invasive surgical procedures such as bypass surgery can be risky and have undesirable side effects.

As such, less invasive surgical devices for constricting or reducing the capacity of the digestive tract, e.g., the stomach, have been developed. These devices include gastric bands which are positioned about the stomach to constrict the stomach. They may also include devices such as inflatable balloons for reducing the reservoir capacity of the stomach. Each of these types of devices produces a sense of satiety in a patient to reduce the patient's desire to ingest food.

Implantation of many of these surgical devices requires access to the exterior of the stomach to secure the device thereabout or therein. Access to the exterior of the stomach may be gained either internally through the stomach wall or externally through the skin and into the abdominal cavity. Accessing the stomach in either of these manners increases the likelihood of infection and other complications both during the procedure and while recovering.

Therefore, it would be beneficial to have a gastric restrictor assembly that may be implanted without having to access the exterior of the stomach.

SUMMARY

According to an aspect of the present disclosure, a gastric restrictor assembly is provided. The gastric restrictor comprises a housing and a base. The housing defines a throughbore and includes a base portion, a waist portion and head portion. The base includes a plurality of pins extending therefrom. The base is configured for being lockingly received within the housing. When received within the housing, the plurality of pins extend across the waist portion of the housing.

The gastric restrictor assembly may further include a restrictor member configured to be received within the throughbore. The base may be releasably received within the housing. The waist portion of the housing may define openings configured for receiving suction therethrough. The base portion of the housing may define openings for receiving the plurality of pins therethrough. The head portion of the housing may define openings for receiving the plurality of pins. The waist portion of the housing may be configured to receive a portion of stomach wall thereagainst. The housing of the gastric restrictor assembly is configured to be received within the stomach of a patient. The housing includes a recessed portion and may define a substantially hourglass figure.

According to another aspect of the present disclosure, a method for restricting a portion of the digestive tract is provided. The method for restricting a portion of the digestive tract includes the steps of positioning a gastric restrictor assembly within a portion of the digestive tract, and lockingly securing the gastric restrictor assembly within the portion of the digestive tract. The assembly includes a housing having a waist portion and defining a throughbore. The housing may further include a base member having a plurality of pins extending therefrom configured to be received within the housing.

The method for restricting a portion of the digestive tract may be performed transorally. The portion of the digestive tract in which the gastric restrictor assembly is positioned may be the stomach. The method may further include the step of providing a restrictor member within the housing to restrict the throughbore. The housing of the gastric restrictor assembly may include a substantially hourglass figure.

BRIEF DESCRIPTION OF THE DRAWINGS

The foregoing summary, as well as the following detailed description will be better understood when read in conjunction with the appended figures. For the purpose of illustrating the present disclosure, a preferred embodiment is shown. It is understood, however, that the present disclosure is not limited to the precise arrangement and instrumentalities shown.

DETAILED DESCRIPTION OF EMBODIMENTS

Figure 1:
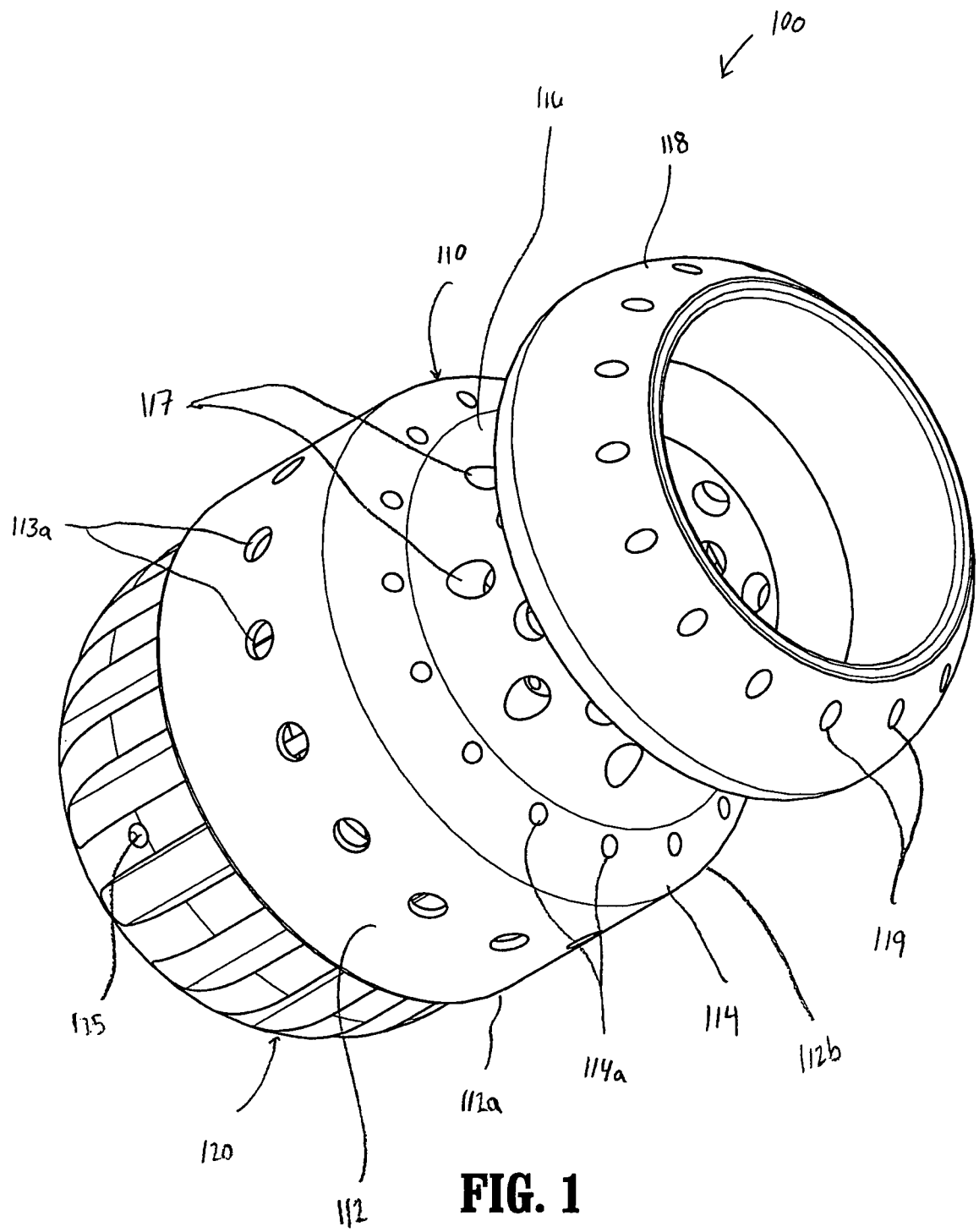
FIG. 1 is perspective side view of an embodiment of a gastric restriction assembly according to present disclosure including a restrictor housing and a pin holder positioned partially within the restrictor housing.
Figure 2:
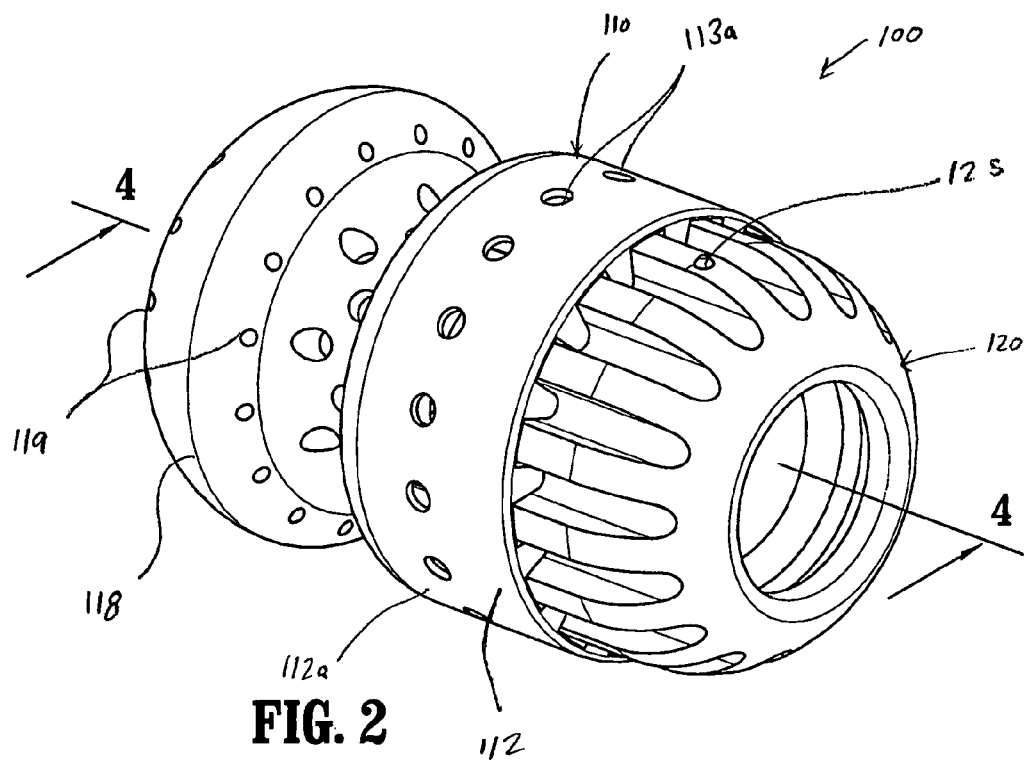
FIG. 2 is an alternate perspective side view of the gastric restriction assembly of FIG. 1.
Figure 3:
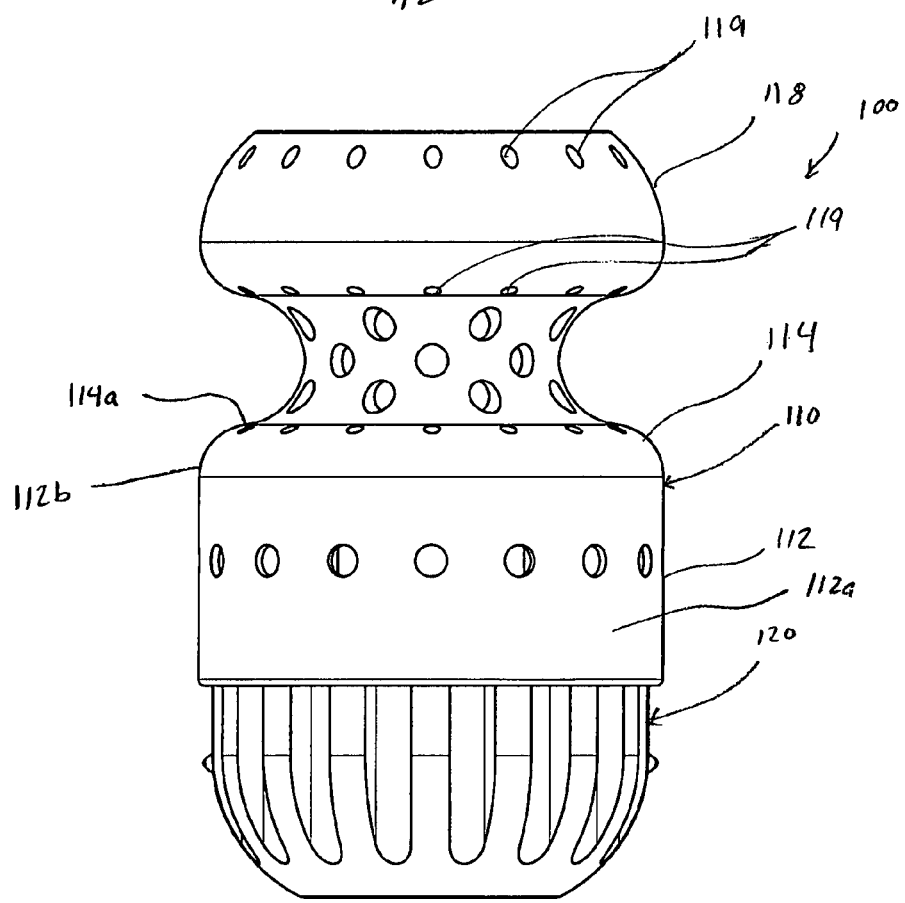
FIG. 3 is a side view of the gastric restriction assembly of FIGS. 1 and 2.

Embodiments of the presently disclosed gastric restrictor assembly and its method of use will now be described in detail with reference to the drawings in which like numerals designate identical or corresponding elements in each of the several views. As shown in the drawings and described throughout the following description, and as is traditional when referring to relative positioning on an object, the term "proximal" refers to the end of the apparatus or device which is closer to the user and the term "distal" refers to the end of the apparatus which is further from the user.

Figure 4:
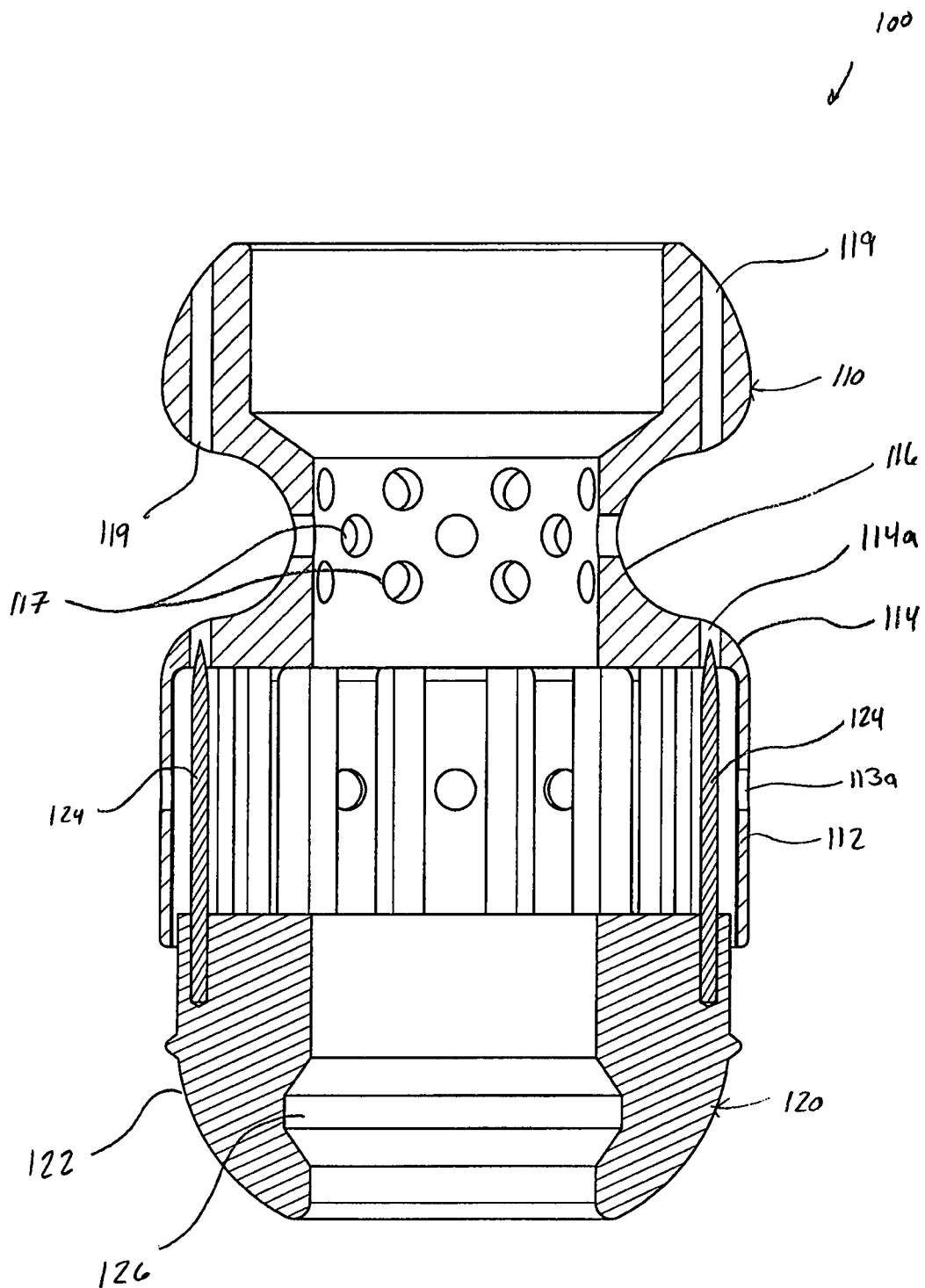
FIG. 4 is a cross-sectional side view of the gastric restrictor assembly of FIGS. 1-3.
Figure 5:
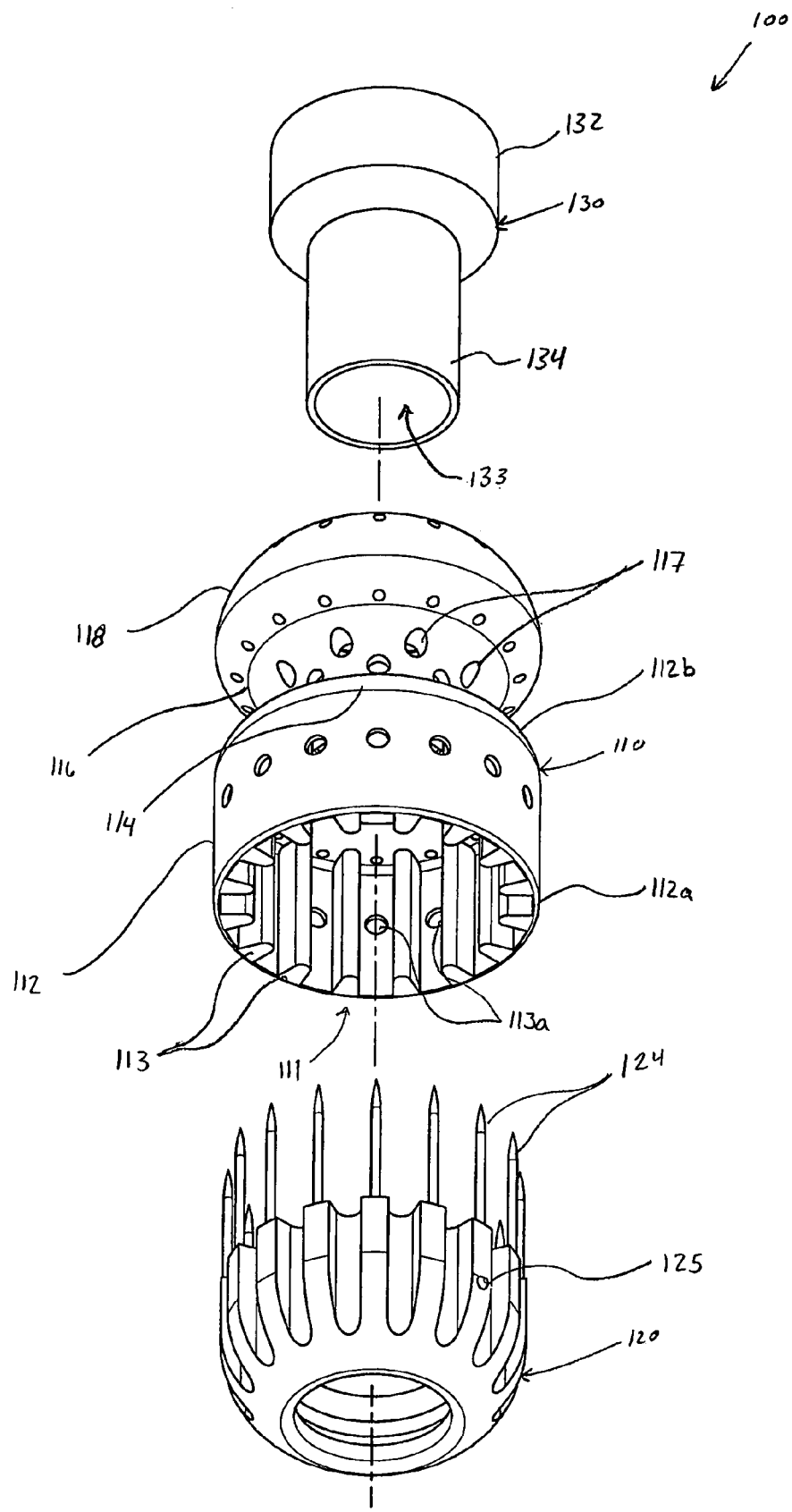
FIG. 5 is an exploded view of the gastric restrictor assembly of FIGS. 1-4, further including a restrictor member.

FIGS. 1-5 illustrate an embodiment of the presently disclosed gastric restrictor assembly, shown generally as restrictor assembly 100. Restrictor assembly 100 includes a restrictor housing 110, a pin holder 120, and a restrictor member 130 (FIG. 5). Gastric restrictor 100 may be configured for non-invasive or minimally invasive implantation within a stomach 10 (FIG. 9) of a patient. Gastric restrictor 100 is maintained within stomach 10 though the use of pins 124, as will be described below. Restrictor assembly 100 is configured to effectively reduce the size of stomach 10. In this manner, a patient may achieve a feeling of fullness after consuming less food then might be required without restrictor assembly 100. Alternatively, assembly 100 may be configured for implanting an artificial sphincter or fastening a shunt into the stomach or intestine.

Referring initially to FIG. 5, restrictor housing 110 includes a base portion 112, a waist portion 116, and a head portion 118. Restrictor housing 110 defines a throughbore 111. Restrictor housing 110 may define a substantially hourglass figure, as shown, or any other configuration having a waist or recessed portion.

Base portion 112 of restrictor housing 110 defines a substantially annular member having an open first end 112a and second end 112b. Open first end 112a is configured for receiving pin holder 120 therein. First end 112a includes internal ridges 113 formed about an inner surface thereof. Ridges 113 are configured for engaging pin holder 120, as will be described below. First end 112a of base portion 112 may further define openings 113a formed between ridges 113. Openings 113a are sized and positioned for lockingly engaging one or more locking tabs 125 disposed on pin holder 130. Second end 112b of base 112 forms a shoulder 114 (FIG. 1) connecting base portion 112 with waist portion 116. Shoulder 114 defines openings 114a therein configured to receive pins 124 therethrough, as will be described below.

Waist portion 116 of restrictor housing 110 connects base portion 112 and head portion 118. Waist portion 116 defines openings 117. As will be described in detail below, openings 117 may form vacuum ports for receiving suction therethrough. As suction is applied through openings 117, stomach 10 (FIG. 9) is restricted thereabout and a portion of stomach wall 12 is received within waist portion 116.

In one embodiment, head portion 118 of restrictor housing 110 forms a substantially mushroom-shaped configuration defining a set of throughholes 119 (FIG. 4). Alternatively, other head portion configurations are envisioned. Throughholes 119 are aligned with openings 114a formed in shoulder 114 on second end 112b of base portion 112. Throughholes 119 are configured to receive pins 124 therein. As will be described below, head portion 118 is further configured to receive restrictor member 130 therein.

Figure 6:
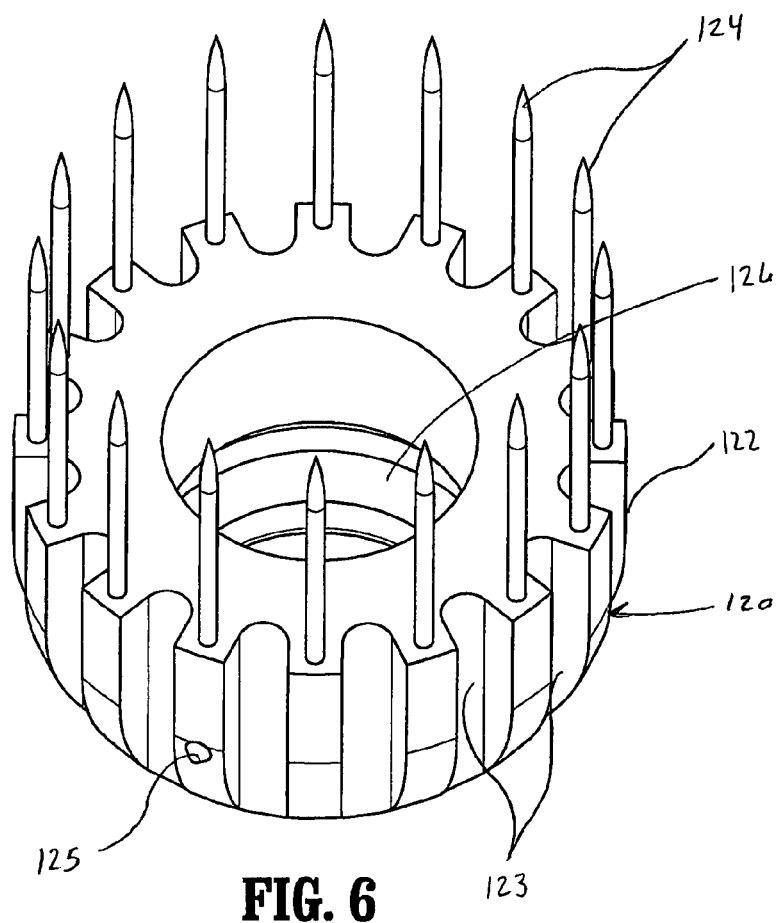
FIG. 6 is a perspective side view of the pin holder of the gastric restrictor assembly of FIGS. 1-5.
Figure 7:
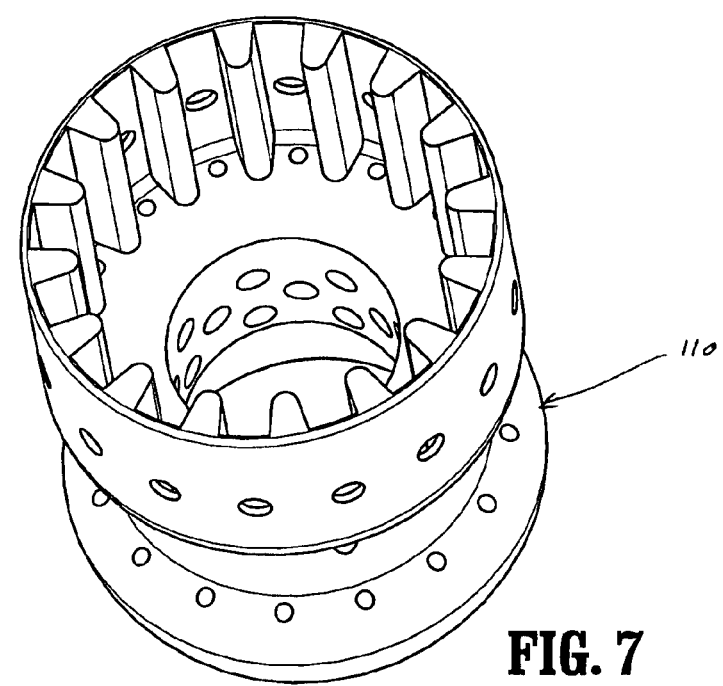
FIG. 7 is a perspective end view of the restrictor housing of the gastric restrictor assembly of FIGS. 1-5.
Figure 15:
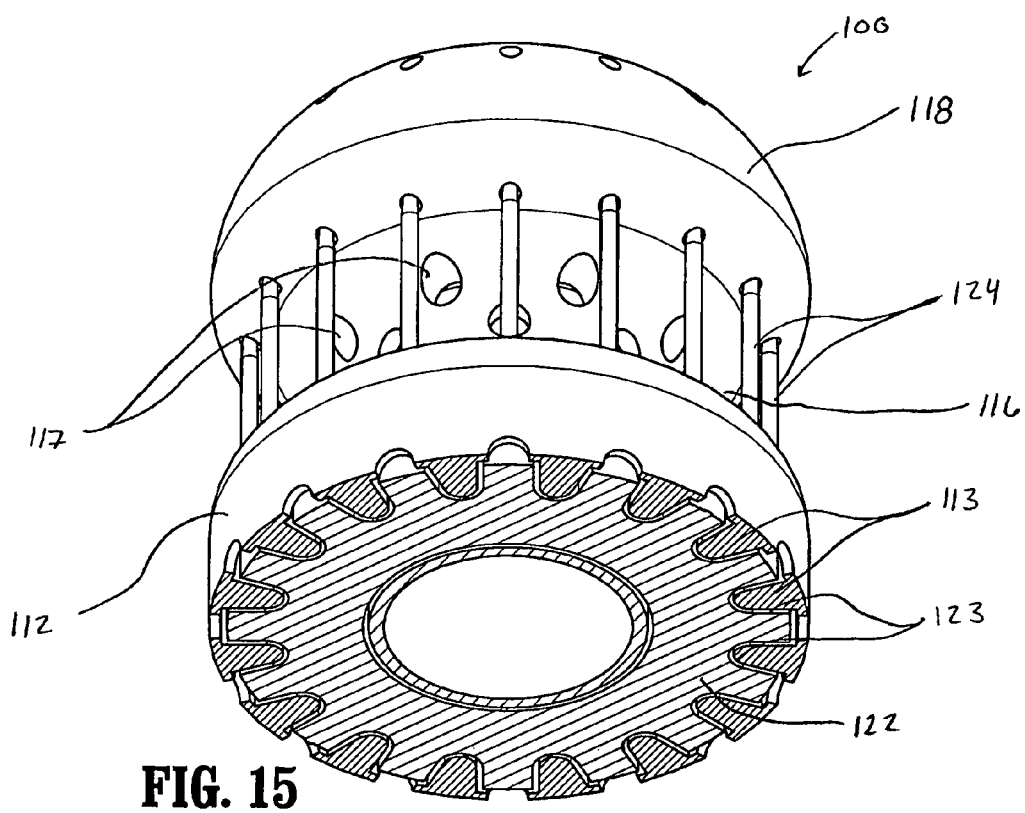
FIG. 15 is a perspective end view of the gastric restrictor assembly of FIGS. 1-5 and 14.

Turning now to FIG. 6, pin holder 120 defines a substantially rigid annular base member 122. Pins 124 extend from a first end 122a of base member 122. Base member 122 further defines grooves 123 formed about an outer surface thereof configured to be matingly received with ridges 113 formed on first end 112a of base portion 112 (FIG. 15). Base member 122 includes one or more locking tabs 125 disposed thereon for selectively locking pin holder 120 within restrictor housing 110. Locking tabs 125 may be biasedly received within base member 122, and are configured to be received within openings 113a formed between ridges 113 in restrictor housing 110. With particular reference to FIG. 4, base member 122 further includes a recess 126 extending about an inner surface thereof. As will be described in further detail below, recess 126 is configured for operable engagement with the operational end of an implantation device.

Turning back to FIG. 5, restrictor member 130 is configured to be received within restrictor housing 110. Restrictor member 130 includes a head portion 132 and a flange portion 134. Both head and flange portions 132, 134 define substantially annular members defining a throughbore 133. In one embodiment, head portion 132 is larger than flange portion 134. It is also envisioned that both head and flange portions 132, 134 may be of equal diameter. Throughbore 133 may increase in diameter within head portion 132, however, a throughbore of constant or varying diameter is envisioned. Throughbore 133 may further define sloped or curved walls for assisting in the passage of material therethrough. As discussed above, assembly 100 may instead incorporate an artificial sphincter or shunt, in which case restrictor member 130 may be replaced with an appropriate member.

With reference now to FIG. 4, head portion 132 of restrictor member 130 is configured to be received within head portion 118 of restrictor housing 110. Flange portion 134 is configured to be received within waist portion 116 of restrictor housing 112. Restrictor member 130 is configured to be selectively removable from within restrictor housing 112. In this manner, restrictor member 130 may be frictionally received within housing 112, or may instead be removably retained within housing 112 using any known securement means including mechanical fasteners, threading, a tongue and groove configuration, magnets, or the like.

Figure 8:
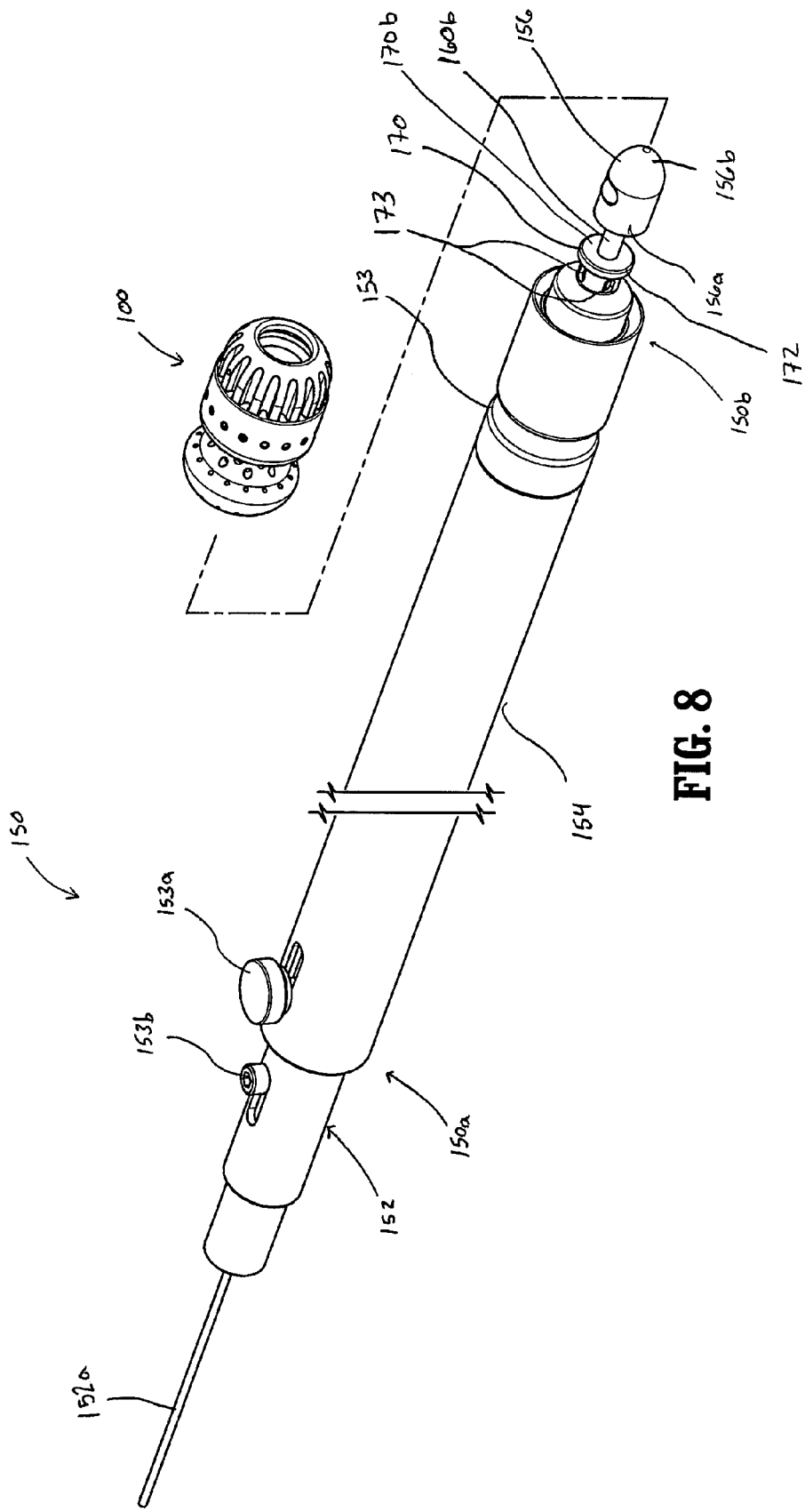
FIG. 8 is a perspective view of an apparatus for implanting the gastric restrictor of FIGS. 1-5.

Gastric restrictor 100 is positioned within the digestive tract of a patient, e.g., the stomach 10 (FIG. 9), using a positioning device. FIG. 8 illustrates an apparatus for positioning gastric restrictor 100 within a digestive tract, shown generally as device 150. Device 150 includes a gripping surface or handle 152 on a proximal end 150a thereof, a tubular body 154, and an operational distal end 150b. Distal end 150b and elongated shaft 154 are configured to be inserted into stomach 10 of a patient through a body opening, e.g., the mouth and esophagus. As will be described in further detail below, gripping surface 152 includes first and second levers or knobs 153a, 153b for actuating operational distal end 150b of device 150.

Figure 10:
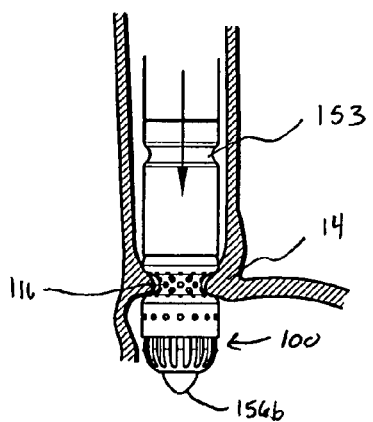
FIG. 10 is a side view of the gastric restrictor assembly and apparatus of FIG. 9, wherein the gastric restrictor assembly has been partially inserted through the cardia sphincter.
Figure 11:
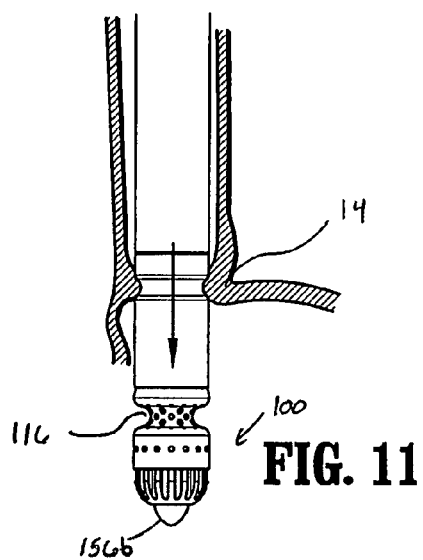
FIG. 11 is a side view of the gastric restrictor assembly and apparatus of FIGS. 9 and 10, wherein the gastric restrictor assembly is completely received within the stomach.
Figure 12:
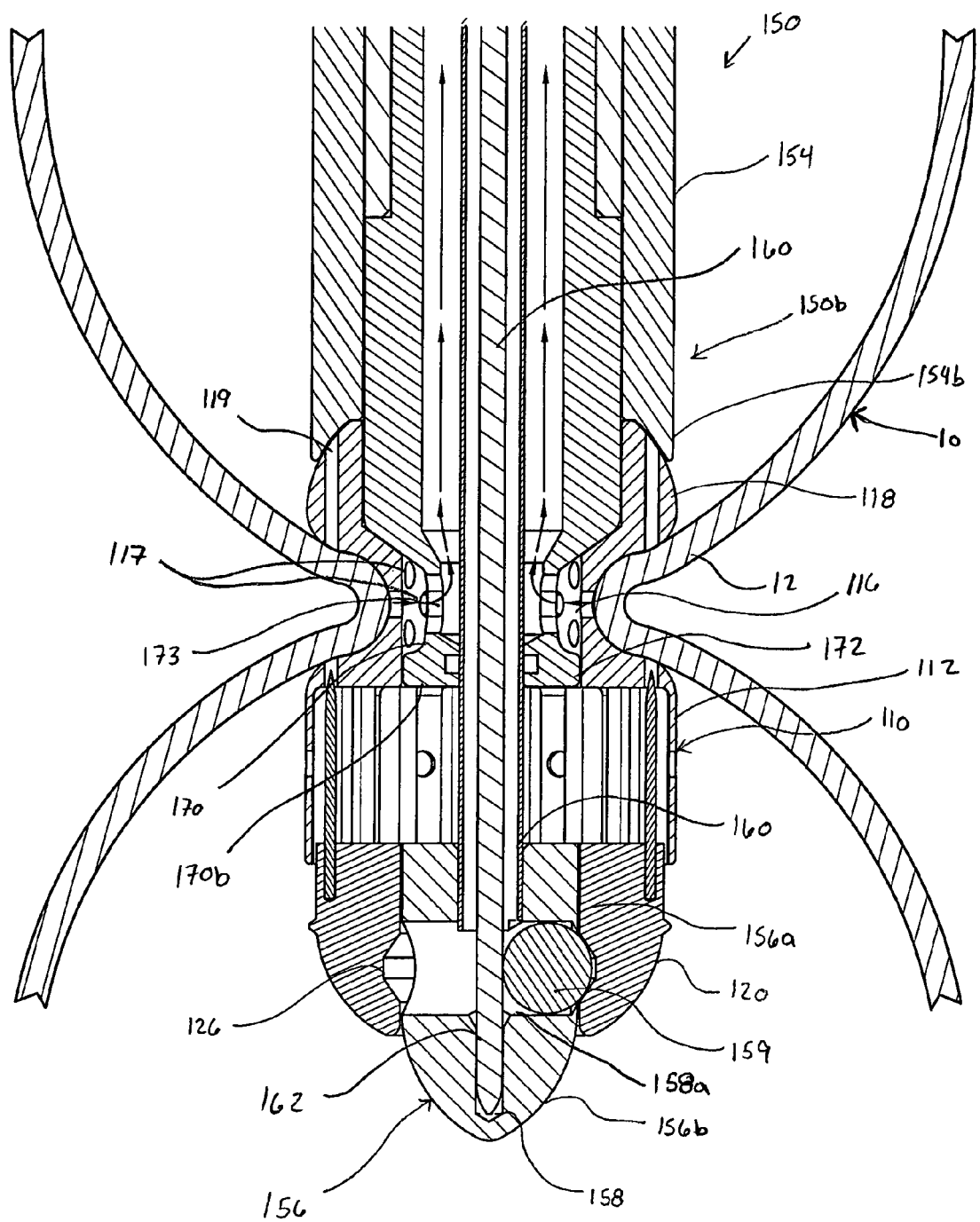
FIG. 12 is a cross-sectional side view of the gastric restrictor assembly and apparatus of FIGS. 9-11, wherein suction provided through the assembly cause the wall of the stomach to be retained thereagainst.

With reference to FIGS. 9-12, distal end 150b of device 150 includes a support member 156 (FIG. 12). Support member 156 includes a proximal end 156a rigidly affixed to a distal end 160b of a shaft 160. Shaft 160 retractably extends from tubular body 154. As will be described in further detail below, shaft 160 is configured to be retracted within tubular body 154 upon actuation of first lever 153a (FIG. 8). Support member 156 further includes a substantially rounded distal end 156b for preventing trauma as distal end 150b of device 150 is inserted into stomach 10 of a patient. Support member 156 is configured to be lockingly received within pin holder 120.

As illustrated in FIG. 12, support member 156 defines a cylindrical recess 158 configured for slidably receiving an engagement pin 162. As will be discussed in further detail below, engagement pin 162 extends from within shaft 160 and is configured to be retracted therein upon actuation of second lever 153b. Support member 156 further includes an opening 158a which extends perpendicular to and is in fluid communication with recess 158. Opening 158 is configured to receive a locking member 159 therein. Locking member 159 is configured to be completely retained within support member 156 when engagement pin 162 is in a first or retracted position. Upon advancement of engagement pin 162 within recess 158 formed in base 122 of pin holder, locking member 159 is configured such that a portion of thereof extends beyond base 122. In this manner, when operational distal end 150b of device 150 is inserted through pin holder 120, advancement of engagement pin 162 causes a portion of locking member 159 to extend within recess 126 formed in base 122 of pin holder 120, thereby locking pin holder 120 about support member 156. Alternatively, support member 156 may instead include any known mechanism for releasably securing pin holder 120 thereto.

With continued reference to FIG. 12, an extension member 170 is disposed between support member 156 and distal end 154b of tubular body 154. Extension member 170 includes a distal end 170b for forming a seal portion 172. Seal portion 172 is configured to be sealingly received within the opening formed in the proximal end 112a of base portion 112 of restrictor member 110. In this manner, base portion 112 may be frictionally received on distal end 150b of device 150. Proximal end 170a of extension member 170 is securely affixed to distal end 154b of tubular body 154. Extension member 170 is configured to permit longitudinal movement of shaft 160 therethrough. Extension member 170 defines a plurality of openings 173 (FIG. 8). As will be discussed in further detail below, openings 173 are configured to correspond with openings 117 defined by waist portion 116 of restrictor housing 110.

Figure 9:
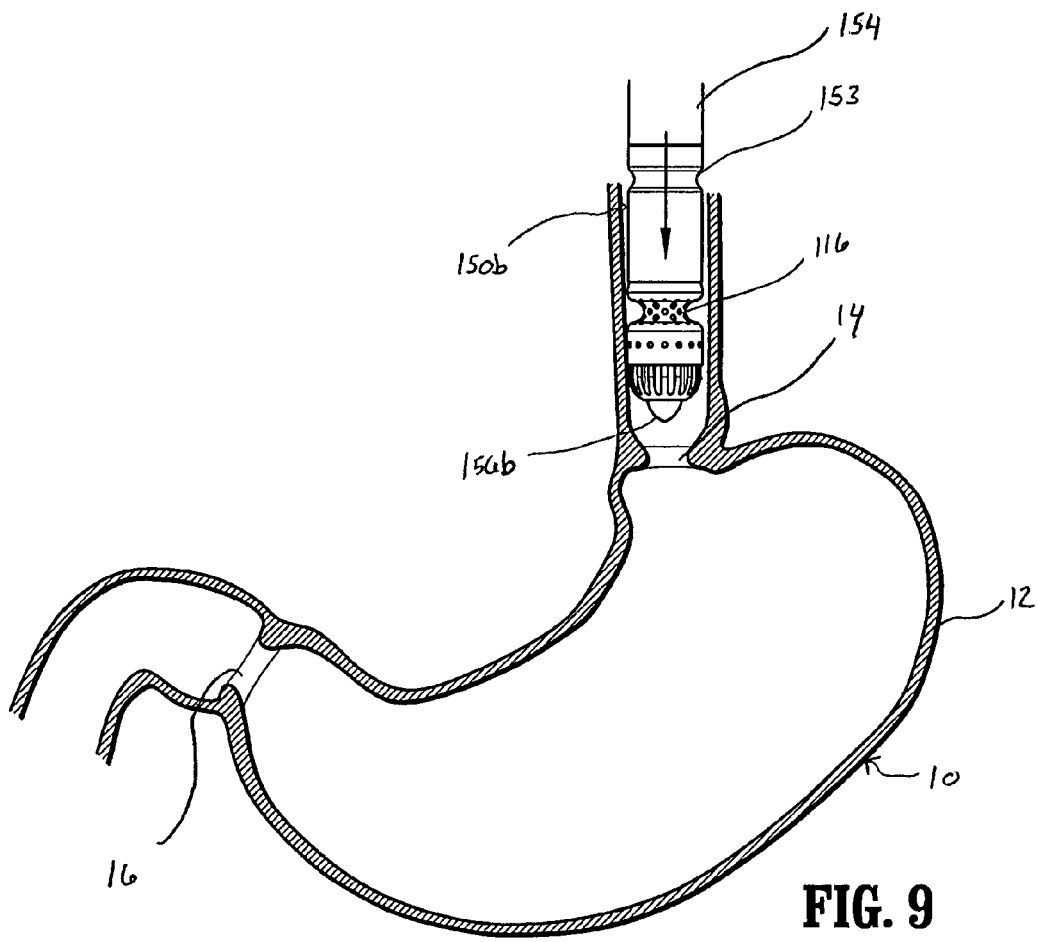
FIG. 9 is side view of a gastric restrictor assembly of FIGS. 1-5 disposed about the distal end of the apparatus of FIG. 8 prior to being introduced though the cardia sphincter of a stomach.

Referring now to FIGS. 8 and 12, distal end 154b of tubular body 154 is configured to operably engage head portion 118 of restrictor housing 112. Restrictor housing 112 may be frictionally engaged with distal end 154b, or instead may be mechanically fastened thereto. Distal end 154b of tubular body 154 further defines a groove or recess 153 thereabout. Depending on the procedure being performed, groove 153 may be configured to engage the cardiac sphincter 14 (FIG. 9) of stomach 10. Groove 153 may be positioned on tubular body 154 such that as distal end 150b of device 150 is inserted though a body opening and into stomach 10, the tactile engagement of cardiac sphincter 14 about groove 153 signifies to the surgeon that gastric restrictor assembly 100 is properly positioned within stomach 10. Tubular body 154 may be of any length, preferably sufficient to permit operational distal end 150b of device 150 to be received within stomach 10 of a patient while gripping surface 152 remains accessible to a surgeon. While tubular body 154 is shown as a rigid member, it is conceivable that tubular body 154 may instead be flexible. Alternatively, tubular body 154 may be configured to position assembly 100 within a small intestine (not shown). In this manner, groove 153 may instead be configured to engage pyloric sphincter 16 (FIG. 9).

With reference to FIGS. 8 and 12, and as discussed above, gripping surface 152 includes first and second levers or knobs 153a, 153b for actuating operational distal end 150b of device 150. First lever 153a is fixedly secured to shaft 160. Retraction of first lever 153a along tubular body 154 causes shaft 160, including support member 156 mounted thereon, to also be retracted. Second lever 153b is fixedly secured to engagement pin 162. Advancement of second lever 153b along tubular body 154 causes the extension of engagement pin 162 with recess 158 formed in support member 156. Although first and second levers 153a, 153b are shown laterally disposed on handle 152 of device 150, it is envisioned that shaft 160 and/or engagement pin 162 may be remotely actuated. Handle 152 is further configured for operable engagement with a source of suction (not shown). Device 150 is connected to the suction source through a hose 152a (FIG. 8). Hose 152a may be integrally formed with device 150 or may instead be releasably connected thereto. Although not shown, handle 152 may further include a button or switch for activating suction at distal end 150b of device 150.

The positioning of gastric restrictor assembly 100 within the digestive tract will now be described with reference to FIGS. 9-13. Initially, restrictor housing 110 is inserted over distal end 150b of device 150. As discussed above, seal portion 172 of extension member 170 is configured to be frictionally received within base portion 112 of restrictor housing 110. In this first or extended condition, shaft 160 is longitudinally spaced from within tubular body 154, while engagement pin 162 is in a retracted position (not shown). With engagement pin 162 in a retracted position, pin holder 120 may be positioned over support member 156. Preferably, shaft 160 is extended relative to tubular body 154 such that when pin holder 120 is positioned over support member 156, pin holder 120 is partially received within body portion 112.

Figure 13:
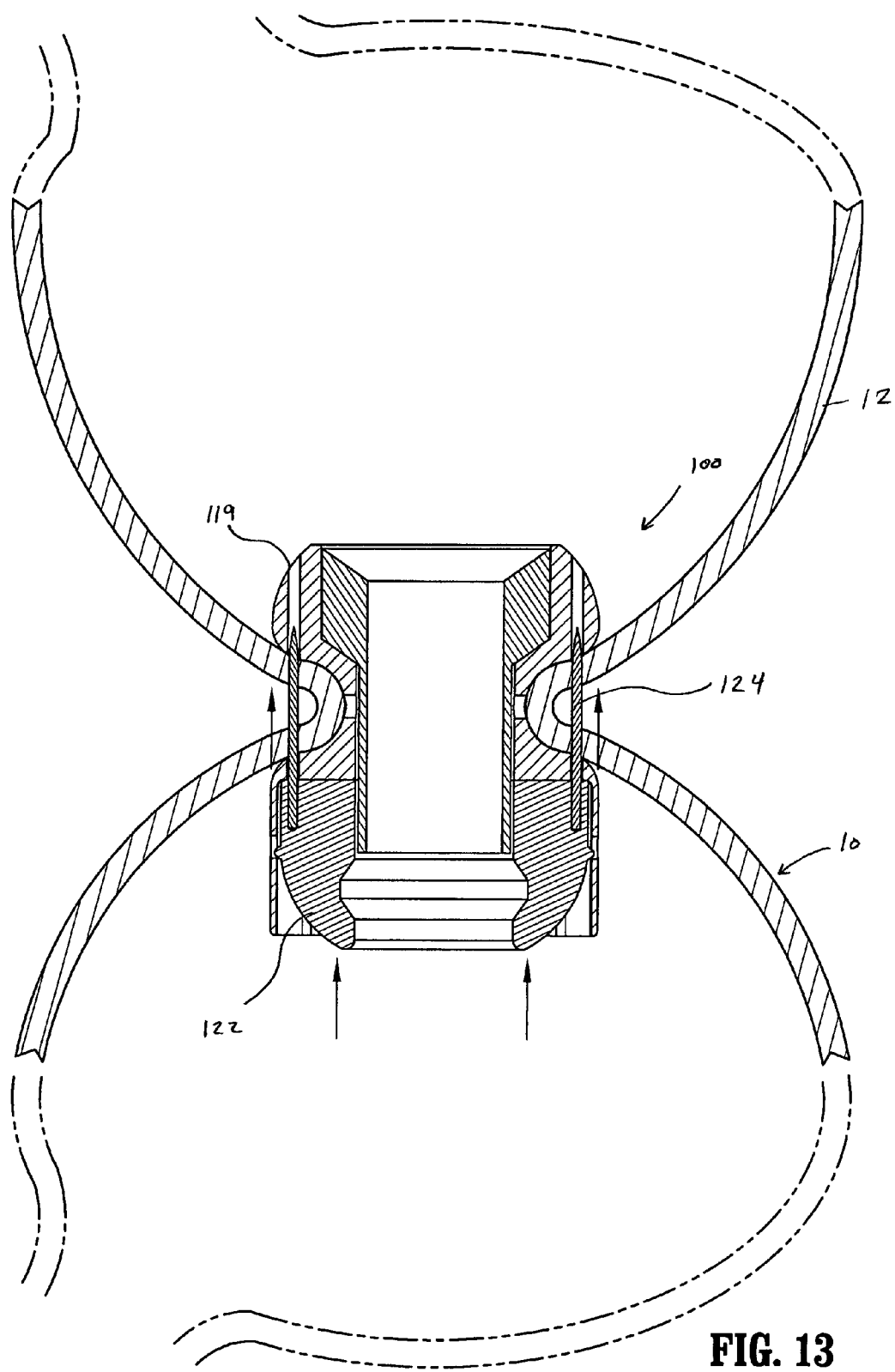
FIG. 13 is a cross-sectional side view of the gastric restrictor assembly of FIGS. 9-12, wherein the pin holder has been lockingly received within the restrictor housing, thereby securing the assembly to the stomach wall.
Figure 14:
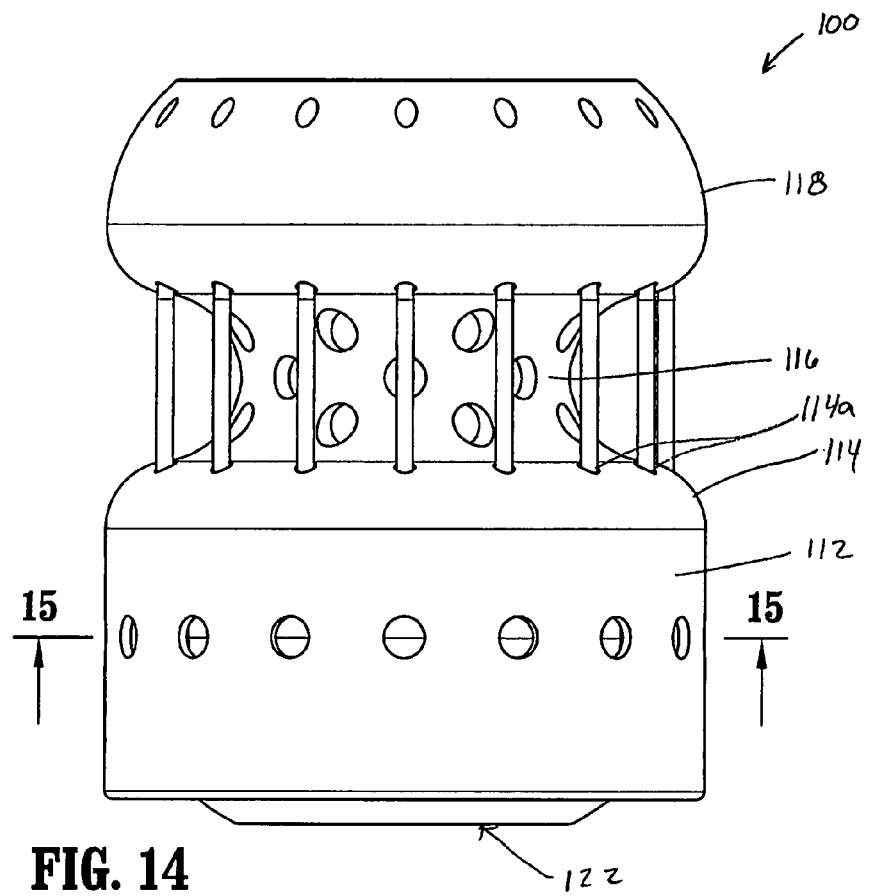
FIG. 14 is the gastric restrictor assembly of FIGS. 1-5, wherein the pin holder has been lockingly received within the restrictor housing.

Once pin holder 120 is positioned over support member 156, engagement pin 162 may be advanced into recess 158 formed in support member 156, thereby partially extending locking member 159 from within opening 158a formed in support member 156. In this manner, locking member 159 extends into recess 126 formed in pin holder 120, thereby locking pin holder 120 to support member 156. With reference to FIG. 12, with shaft 160 still in the first or extended position, pin holder 120 is partially received within second end 112b of base 112. Engagement of ridges 113 formed in the inner surface of restrictor housing 110 with grooves 123 formed on the outer surface of pin holder 120 causes the alignment of pins 124 with openings 114a defined by shoulder 114 formed in proximal end 112a of base portion 112. Retraction of shaft 160 within tubular body 154 results in the retraction of pin holder 120 within restrictor housing 110 and extension of pins 124 across waist portion 114 of restrictor housing 110 (FIG. 13).

With restrictor housing 110 releasably secured to distal end 154b of tubular body 154, shaft 160 in an extended condition relative to tubular body 154, and pin holder 120 releasably secured about support member 156, gastric restrictor assembly 100 is loaded and ready for implantation. With initial reference to FIG. 9, once inserted through the body orifice and directed through the esophagus 20 of a patient, rounded distal end 156b of support member 156 engages cardiac sphincter 14. Engagement of cardiac sphincter 14 by support member 156 signals to a surgeon the position of distal end 150b of device 150 relative to stomach 10.

Further advancement of device 150 causes gastric restrictor assembly 100 to open cardiac sphincter 14 and begin to be passed therethrough. Device 150 may continue to be advanced until cardiac sphincter 14 engages waist portion 114 of restrictor housing 112 (FIG. 10). The tactile response felt by the surgeon upon engagement of waist portion 114 with cardiac sphincter 14 further signals to the surgeon the position of gastric restrictor assembly 100. Distal end 150b of device 150 may continue to be advanced into the patient until a third tactile response is felt by the surgeon. This third tactile response signals to the surgeon that cardiac sphincter 14 has engaged groove 153 formed in tubular body 154 (FIG. 11). As discussed above, groove 153 is preferably positioned such that upon engagement of cardiac sphincter 14 with groove 153, gastric restrictor assembly 100 is properly positioned within stomach 10 and is ready to be releasably secured therein.

With reference back to FIG. 12, when suction is supplied to device 150, a vacuum is created within stomach 10 causing a portion of wall 12 thereof to be suctioned against waist portion 116 of restrictor housing 110. Suction of wall 12 against waist portion 116 effectively divides stomach 10 into two sections (FIG. 13). Gastric restrictor assembly 100 may be securely retained to stomach wall 12 and within stomach 10 upon actuation of first lever 153a. Retraction of first lever 153a causes retraction of shaft 160. Retraction of shaft 160 causes support member 156 and pin holder 120, mounted thereon, to be retracted within restrictor housing 110. Pins 124 extending from pin holder 120 are thereby received through openings 113 formed in second end 112a of base portion 112, are extended across waist portion 116, and are received within throughholes 119 defined in head portion 118. In this manner, stomach wall 12 is pierced by and retained in position about waist portion 114 by pins 124. Locking tabs 125 are received within openings 113a formed between ridges 113 formed in base portion 112 (FIG. 13) to secure assembly 100 within stomach 10.

Alternatively, and in an invasive procedure, stomach wall 12 may be restricted about waist portion 116 of restrictor housing 110 with a suture, string or the like wrapped around the outside surface of stomach 10.

The configuration and operation of gastric restrictor assembly 100 coupled with the anatomy of stomach 10 enables pins 124 extending from pin holder 120 to pass thru the weaker mucosal layer of the stomach and grip the tough muscular layer of the stomach beneath the mucosal layer, while sparing the outer cerosal layer. Furthermore, the multiple pin spacing can be controlled far more precisely than with hand suturing. This provides a superior anchoring of gastric restrictor assembly 100 to stomach wall 12. This is particularly important in barriatric cases where overeating by a patient may place substantial stress on the anchoring means.

Once pin holder 120 has been lockingly received within restrictor housing 110 and gastric restrictor assembly 112 has been secured to and within stomach 10, device 150 may be removed. To disengage support member 156 from within pin holder 120, second lever 153b is retracted along handle 152, thereby retracting engagement pin 162. Retraction of engagement pin 162 permits disengagement of locking member 159 from within recess 126 formed in restrictor housing 110. Support member 156 is thus disengaged from pin holder 120, thereby permitting distal end 150b of device 150 to be retracted from within gastric restrictor assembly 100 and stomach 10.

It will be understood that various modifications may be made to the embodiments disclosed herein. Therefore, the above description should not be construed as limiting, but merely as exemplifications of embodiments. Those skilled in the art will envision other modifications within the scope and spirit of the claims appended hereto. In addition to the described gastric restriction procedure and other procedures easily envisioned by those of ordinary skill in the art, the embodiments of the present disclosure may be modified for providing an artificial sphincter or fastening a shunt into the stomach or intestine.

What is claimed is:

1. A gastric restrictor assembly comprising:
    a housing including a base portion, a waist portion and a head portion, wherein the base portion, the waist portion and the head portion are of unitary construction and the housing defines a throughbore;
    a pin holder including a plurality of pins extending therefrom, the pin holder configured for being lockingly received within the housing, wherein the plurality of pins are supported by the pin holder to extend across the waist portion when the pin holder is received within the base portion of the housing.

2. The gastric restrictor assembly of claim 1, further including a restrictor member configured to be received within the throughbore.

3. The gastric restrictor assembly of claim 1, wherein the pin holder is releasably received within the housing.

4. The gastric restrictor assembly of claim 1, wherein the waist portion of the housing defines openings configured for receiving suction therethrough.

5. The gastric restrictor assembly of claim 1, wherein the base portion of the housing defines openings for receiving the plurality of pins therethrough.

6. The gastric restrictor assembly of claim 1, wherein the head portion of the housing defines openings for receiving the plurality of pins.

7. The gastric restrictor assembly of claim 1, wherein the waist portion of the housing is configured to receive a portion of stomach wall thereagainst.

8. The gastric restrictor assembly of claim 1, wherein the housing is configured to be received within the stomach of a patient.

9. The gastric restrictor assembly of claim 1, wherein the housing defines a substantially hourglass figure.

10. The gastric restrictor assembly of claim 1, wherein a first end of the housing includes ridges formed about an inner surface thereof.

11. The gastric restrictor assembly of claim 10, wherein the pin holder includes ridges formed about an outer surface thereof configured to engage the ridges formed on the housing when the pin holder is received within the throughbore of the housing.

12. The gastric restrictor assembly of claim 1, wherein the pin holder includes one or more locking tabs for selectively engaging the housing when the pin holder is received with the open distal end of the housing.

13. The gastric restrictor assembly of claim 1, wherein the waist portion defines a plurality of openings.

14. The gastric restrictor assembly of claim 1, wherein the head portion forms a substantially mushroom-shaped configuration.

15. The gastric restrictor assembly of claim 1, wherein the pins are disposed radially outward of the waist portion when the pin holder is received within the base portion of the housing.

16. A gastric restrictor assembly comprising:
    a housing including a base portion, a waist portion and a head portion, the housing defining a throughbore;
    a pin holder including a plurality of pins extending therefrom, the pin holder configured for being lockingly received within the housing, wherein the plurality of pins are disposed radially outward of the waist portion when the pin holder is received within the base portion of the housing;
    wherein the restrictor is configured to capture a portion of gastric tissue radially inward of the pins and radially outward of the waist portion.

* * * * *